United States Patent
Wiley

(10) Patent No.: US 6,444,220 B2
(45) Date of Patent: Sep. 3, 2002

(54) METHOD AND COMPOSITIONS FOR CHANGING THE CONTOUR OF SKIN

(76) Inventor: Teresa S. Wiley, 1620 Eucalyptus Hill Rd., Santa Barbara, CA (US) 93103

( * ) Notice: Subject to any disclaimer, the term of this patent is extended or adjusted under 35 U.S.C. 154(b) by 0 days.

(21) Appl. No.: 09/910,413

(22) Filed: Jul. 20, 2001

Related U.S. Application Data

(63) Continuation-in-part of application No. 09/527,178, filed on Mar. 16, 2000, now abandoned.

(51) Int. Cl.$^7$ .................................................. A61K 9/70
(52) U.S. Cl. ........................ 424/449; 424/401; 424/443; 424/447; 514/3; 514/171
(58) Field of Search ................................. 424/401, 443, 424/449, 447; 514/3, 171

(56) References Cited

U.S. PATENT DOCUMENTS 6,024,975 A * 2/2000 D'Angelo et al. .......... 424/449

* cited by examiner

Primary Examiner—Jose' G. Dees
Assistant Examiner—Konata M. George
(74) Attorney, Agent, or Firm—Michael G. Petit

(57) ABSTRACT

Compositions containing insulin formulated for topical application and a method for using the compositions for the cosmetic treatment of wrinkles. The formulation is useful for contouring the skin for the reduction of wrinkles, furrows and the like. Insulin, delivered transdermally by means of topical application to a portion of skin having wrinkles and/or furrows therein, permeates the epidermis and accumulates in the dermis and subcutaneous tissue underlying the portion of skin. The elevated insulin concentration in the dermis and subcutaneous tissue, relative to the concentration of insulin in other analogous, remotely located tissue, typically in the range of about 25–50 $\mu$U/gm, stimulates the formation of a layer of adipose tissue in the insulin-rich tissue underlying the portion of skin. The fatty tissue thus formed exerts pressure on the overlying, relatively elastic portion of skin thereby stretching the skin and reducing the depth of wrinkles therein and improving the cosmetic appearance of the skin.

6 Claims, No Drawings

METHOD AND COMPOSITIONS FOR CHANGING THE CONTOUR OF SKIN

This is a continuation-in-part of Ser. No. 09/527,178 filed Mar. 16, 2000, now abandoned.

BACKGROUND OF THE INVENTION

1. Field of the Invention

A dermatological composition comprising insulin and a method for using the composition for the treatment of wrinkles.

2. Prior Art

Insulin is a naturally occurring hormone secreted by the beta cells of the islands of Langerhans in the pancreas in response to increased levels of glucose in the blood. The hormone acts to regulate the metabolism of glucose and the processes associated with the intermediary metabolism of fat, carbohydrates and proteins. Insulin lowers blood glucose levels and promotes transport and entry of glucose into muscle cells and other tissues. Due to the chemical nature of insulin molecule, the traditional route of insulin administration in Type 1 diabetic patients, who require multiple daily doses of insulin, is intradermal or subdermal injection, It is well known that Type 1 diabetics form "fat pads" at sites receiving multiple injections of insulin. It is less known that some patients receiving multiple, chronic, subcutaneous injections of insulin, develop a condition known as insulin lipodystrophy wherein fat deposits are lost at the site of multiple injections. Prior art efforts to develop a non-injectable transdermal insulin delivery system for the treatment of Type 1 diabetes have not been successful to date. While insulin can be systemically delivered to a patient by the topical application of an insulin-containing vehicle, the systemic blood levels of insulin that are achievable using this delivery method have proven to be generally inadequate for meeting the demands of the Type 1 diabetic patient. The present invention focuses attention on identifying medical conditions other than diabetes that can be treated successfully by the localized perfusion of dermal and subcutaneous tissue with low levels of insulin using topical insulin formulations.

Methods developed for enhancing the transdermal delivery of insulin include improved passive diffusion carriers for increasing the permeability of the epidermis, sonophoresis, iontophoresis and ionosonic transport. Passive diffusion through the outer layer of skin has been used successfully for the delivery of low molecular weight lipophilic drugs such as scopolamine, estradiol and nitroglycerine, but has been largely unsuccessful for the transdermal delivery of hydrophilic peptides such as insulin due to the low skin permeability of such peptides. Accordingly, mechanical vibrational energy and/or iontophoresis are employed to increase skin permeability and facilitate transdermal insulin delivery. Sibalis et al., in U.S. Pat. No. 4,940,456, teaches an apparatus and method for the iontophoretically mediated transdermal delivery of insulin. Henley, in U.S. Pat. Nos. 5,667,487 and 5,658,247 discloses an ionosonic apparatus suitable for the ultrasonic-iontophoretically mediated transport of therapeutic agents across the skin. Insulin has a tendency to form dimers and hexamers in pharmacological compositions, which are considered to be too large for transdermal delivery. Brange, in U.S. Pat. No. 5,597,796, suggests chemically modifying insulin to produce insulin analogs that resist intermolecular association and enable improved iontophoretic delivery. Jang et al., in U.S. Pat. No. 5,681,580, discloses a patch containing insulin formulated in a gel for the iontophoretically driven transdermal delivery of insulin.

Leidtke, in European patent EP0561330 A1, teaches the use of topically applied compositions comprising insulin to accelerate wound healing. Leidtke lacks teaching of a composition for removing irregularities in the contour of a portion of skin wherein the irregularities are attributable to anything other than a wound. In particular, there is no suggestion in Leidtke of using such compositions for treating any skin condition other than wounds.

Notwithstanding the advances in methods for the transdermal delivery of insulin described above, a student of the prior art will acknowledge that the transdermal delivery of insulin in a quantity sufficient to attain a therapeutic level in the blood of diabetic patients is, at present, difficult, if not impossible. Nevertheless, the prior art has clearly demonstrated that the topical application of a formulation containing insulin can and does produce measurable levels of insulin in the blood. In order to enter the blood, the insulin must penetrate the stratum corneum and enter the dermis and subcutaneous tissue wherein lie the capillaries through which the insulin enters the blood stream. It is reasonable to postulate that the concentration of insulin in non-vascular tissue underlying the area of transdermal penetration is higher than in surrounding tissue, or in the same tissue disposed at a location remote from the area of transdermal penetration, and that the ability to produce such a differentially higher level of insulin in selected dermal and/or subdermal tissue, may have therapeutic or cosmetic uses. The justifiable focus of the prior art on the use of insulin for treating diabetes or for accelerating wound healing has diverted efforts to explore other, less important medical applications.

SUMMARY OF THE INVENTION

The present invention discloses a method for recontouring intact skin such as for the treatment of wrinkles in the skin. The method employs topical administration or intradermal injection of insulin to a portion of skin containing wrinkles in order to establish a high intradermal and/or subcutaneous concentration of insulin in or underlying the portion of skin. The insulin induces the formation of fatty tissue in tissue underlying the wrinkle(s) thereby smoothing the contour of the portion of skin comprised of wrinkles.

It is a first object of the invention to provide a method and composition for the cosmetic treatment or minimization of unwanted contours in the skin such as wrinkles.

It is a further object of the invention to provide a composition and method for the transdermal delivery of insulin to selective tissue underlying a portion of intact skin in a quantity sufficient to cause localized fat pads to form beneath the portion of skin.

Living mammalian skin is elastic as can be observed in, for example, the skin overlying the uterus of a female in the latter stage of pregnancy. The purpose of forming fat pads under the skin by the infusion of insulin in accordance with the present invention is to stretch the elastic skin overlying the fat pad thereby reducing wrinkle depth in the skin overlying the fat pad.

The features of the invention believed to be novel are set forth with particularity in the appended claims. However, the invention itself, both as to organization and method of operation, together with further objects and advantages thereof, may be best be understood by reference to the following description of the preferred embodiments.

DESCRIPTION OF THE PREFERRED EMBODIMENTS

The skin of a person comprises an outer layer of epidermis and an underlying layer of dermis. The term "transdermal drug delivery", as used herein, means the transport of a drug into the dermis when the drug is topically applied to the epidermis of the skin. If the drug is insulin, any means whereby insulin may be transdermally delivered, and any composition containing insulin, which may be transdermally, delivered by such insulin transdermal delivery means, may be employed to practice the method presented herein for minimizing wrinkles in the skin. Thus, compositions comprised of insulin which may be used to practice the present invention include lotions, ointments, creams and gels formulated for topical application. Transdermal delivery of the insulin comprising the composition may be by passive diffusion or be facilitated by physical means such as applying ultrasound or an electrical current to the portion of skin supporting the insulin-containing composition. In addition, the insulin in the composition may be contained within a liposome or similar lipophilic carrier suspended in an appropriate vehicle.

One such composition containing insulin and formulated for transdermal delivery is disclosed by Gertner et al in U.S. Pat. No. 5,707,641. The formulation is an aqueous emulsion or dispersion comprising an aqueous phase, insulin, an emulsifier and an oil phase. A suitable oil phase comprises an ester made from an aliphatic alcohol or polyol such as glycerol, containing 1–4 hydroxyl groups, and an aliphatic carboxylic acid containing 8–24 carbon atoms and 1–3 carboxyl groups such as palmitic or stearic acid. The oil phase may comprise or consist essentially of natural fats or oils such as almond, olive, linoleic and/or peanut oil, which are a mixture of different esters having the required properties for the oil phase.

A formulation suitable for the transdermal delivery of insulin, either alone or with estradiol, is made as follows. One gram of lecithin powder (and, if desired, about 25 mg estradiol) is added to six ml of aqueous insulin solution containing about 100 U of insulin/ml (Novo Nordisk A/S) and the mixture is stirred rapidly at 35 degrees centigrade for ninety minutes. Four ml of fractionated coconut oil (Unichem Ltd) is added to the insulin-lecithin mixture and stirring is continued at 35 degrees centigrade for an additional 90 minutes. The resulting emulsion may be further treated by sonication for two minutes. Gertner (i.b.i.d.) suggests pretreating the insulin solution by letting it remain at room temperature for 30 days (which may be followed by refrigeration for 60 days) prior to use, in order to minimize hexamer formation and enhance delivery. The composition is administered repetitively until the formation of fat pads beneath the skin is sufficient to provide the desired cosmetic result.

A further composition formulated for topical application and transdermal delivery of insulin in accordance with the present invention contains about 2.5 mg/ml estradiol and about 10–1000 U/ml insulin. Humulin, a genetically engineered form of human insulin, is preferably used. The forgoing active agents are preferably contained within lipophilic liposomes dispersed in a suitable biphasic vehicle. The composition may further comprise an emulsifier such as lecithin. As described above, the composition is administered repetitively until the formation of fat pads beneath the skin is sufficient to provide the desired cosmetic result.

In summary, the present invention generally discloses a method for changing the surface contour of an intact, wound-free portion of skin. The method comprises the step of applying a composition containing insulin as an essential ingredient to the surface of the skin. The insulin-containing composition is formulated to permit the transdermal delivery of insulin either with or without the use of adjunctive delivery means such as iontophoresis. More particularly, the present invention discloses a method for reducing the depth of wrinkles in a wound-free portion of skin. The method comprises the step of applying a composition containing essentially insulin to the outermost surface of the portion of skin. The insulin-containing composition is formulated to permit the transdermal delivery of insulin, either with or without the assistance of udjunctive instrumentation. The step of applying the composition to the skin is repeated until a desired reduction in the depth of the wrinkles in the portion of skin is achieved While particular embodiments of the present invention have been illustrated and described, it would be obvious to those skilled in the art that various other changes and modifications can be made without departing from the spirit and scope of the invention.

For example, insulin may be injected into or under a portion of skin bearing wrinkles to induce the formation of fat pads and remove the onerlying wrinkles. It is therefore intended to cover in the appended claims all such changes and modifications that are within the scope of this invention.

What I claim is:

1. A method for changing the surface contour of a wound-free portion of skin comprising the step of applying a composition containing insulin as an essential ingredient to the skin wherein said composition is formulated to permit the transdermal delivery of insulin.

2. The method of claim 1 wherein said composition further comprises estradiol.

3. The method in accordance with claim 1 wherein said step of applying a composition containing insulin to the skin is repeated until a desired skin contour is achieved.

4. The method in accordance with claim 2 wherein said step of applying a composition containing insulin and estradiol to the skin is repeated until a desired skin contour is achieved.

5. A method for reducing the depth of wrinkles in a wound-free portion of skin, the method comprising the step of applying a composition containing insulin as an essential ingredient to the outermost surface of the portion of skin, said composition being formulated to permit the transdermal delivery of insulin, said step of applying being repeated until a desired reduction in the depth of the wrinkles in the portion of skin is achieved.

6. The method of claim 5 wherein said composition further comprises estradiol.

* * * * *